(12) United States Patent
Charych et al.

(10) Patent No.: US 6,183,772 B1
(45) Date of Patent: *Feb. 6, 2001

(54) DOPED COLORIMETRIC ASSAY LIPOSOMES

(75) Inventors: Deborah Charych; Raymond C. Stevens, both of Albany, CA (US)

(73) Assignee: The Reagents of the University of California, CA (US)

(*) Notice: Under 35 U.S.C. 154(b), the term of this patent shall be extended for 0 days.

This patent is subject to a terminal disclaimer.

(21) Appl. No.: 08/609,312

(22) Filed: Mar. 1, 1996

Related U.S. Application Data

(63) Continuation-in-part of application No. 08/389,475, filed on Feb. 13, 1995, now abandoned.

(51) Int. Cl.[7] .......................... A61K 9/127; A61K 49/00; G01N 33/53; G01N 33/544
(52) U.S. Cl. .................... 424/450; 424/9.51; 424/210.1; 424/396; 424/812; 935/54; 436/528; 436/531; 436/829; 427/2.14; 435/4; 435/9; 435/6; 435/7.1
(58) Field of Search ............................... 435/4, 9, 6, 7.1; 422/55, 57–58, 82.05; 436/528, 531, 501, 829; 427/2.14; 428/441, 462; 424/450, 396, 9.51, 283.1, 812, 210.1; 935/54

(56) References Cited

U.S. PATENT DOCUMENTS

| | | |
|---|---|---|
| 4,859,538 | 8/1989 | Ribi . |
| 5,268,305 | * 12/1993 | Ribi et al. .............................. 436/501 |
| 5,415,999 | 5/1995 | Saul et al. . |
| 5,427,915 | 6/1995 | Ribi et al. . |
| 5,491,097 | 2/1996 | Ribi et al. . |
| 5,521,101 | 5/1996 | Saini et al. . |
| 5,571,568 | 11/1996 | Ribi et al. . |
| 5,618,735 | 4/1997 | Saul et al. . |
| 5,622,872 | 4/1997 | Ribi . |

OTHER PUBLICATIONS

Arisawa et al., "Quantitative characterization of enzymes adsorbed on to Langmuir–Blodgett films and the application to a urea sensor," *Thin Solid Films* 210:443–445 (1992).
Beswick et al., "Optical Detection of Toxic Gases Using Fluorescent Porphyrin Langmuir–Blodgett Films," *J. Colloid Interface Sci.* 124:146–155 (1988).
Chance et al., "Thermal effects on the optical properties of single crystals and solution–cast films of urethane substituted polydiacetylenes," *J. Chem. Phys.* 71:206–211 (1979).
Cuatrecasas, "Interaction of Vibrio cholerae Enterotoxin with Cell Membranes," *Biochemistry* 12: 3547–3558 (1973).
Frankel et al., "Supramolecular Assemblies of Diacetylenic Aldonamides," *J. Am. Chem. Soc.* 116: 10057–10069 (1994).
Furuki et al., "Hybrid gas detector of squarylium dye Langmuir–Blodgett film deposited on a quartz oscillator,"0 *Thin Solid Films* 210:471 (1992).
Kaneko et al., "Absorption properties and structure changes caused by pre–annealing in polydiacetylene Langmuir–Blodgett films," *Thin Solid Films* 210:548–550 (1992).
Kingery–Wood et al., "The Agglutination of Erythrocytes by Influenza Virus is Strongly Inhibited by Liposomes Incorporating an Analog of Sialyl Gangliosides," *J. Am. Chem. Soc.* 114:7303–7305 (1992).
Kuo et al., "Synthesis and Properties of Diacetylenic Glutamate Lipid Monomer and Polymer: Thermochromic Polydiacetylene Free–Standing Films," *Macromolecules* 23:3225–3230 (1990).
Mino et al., "Photoreactivity of 10,12–Pentacosadiynoic Acid Monolayers and Color Transitions of the Polymerized Monolayers on an Aqueous Subphase," *Langmuir* 8:594–598 (1992).
Miyasaka et al., "Amperometric Glucose Sensor with Glucose Oxidase Immobilized on $SnO_2$ Electrode via a Monolayer of a Photoreactive Nitrophenylazide Derivative,"0 *Chem. Lett.*, pp. 627–630 (1990).
Novotny et al., "Tribology of Langmuir–Blodgett Layers," *Langmuir* 5:485–489 (1989).
Okahata et al., "Preparation of Langmuir–Blodgett Films of Enzyme–Lipid Complexes: A Glucose Sensor Membrane," *Thin Solid Films* 180:65–72 (1989).
Ott et al., "Liposomes and influenza viruses as an in vitro model for membrane interactions II. Influence of vesicle size and preparation methods," *Eur. J. Pharm. Sci.* 6:333–341 (1994).
Reichert et al., "Polydiacetylene Liposomes Functionalized with Sialic Acid and Colorimetrically Detect Influenza Virus," *J. Am. Chem. Soc.* 117:829–830 (1995).
Rhodes et al., "Structure of Polymerizable Lipid Bilayers. 6. Bilayer Structure of Three Polymerizable Diacetylenic Glutamate Lipids," *Langmuir* 10:267–275 (1994).
Shibata, "Reversible Colour Phase Transitions and Annealing Properties of Langmuir–Blodgett Polydiacetylene Films," *Thin Solid Films* 179:433–437 (1989).
Spevak et al., "Polymerized Liposomes Containing C–Glycosides of Sialic Acid: Potent Inhibitors of Influenza Virus in Vitro Infectivity," *J. Am. Chem. Soc.* 115: 1146–1147 [1993].

(List continued on next page.)

*Primary Examiner*—Keith D. MacMillan
*Assistant Examiner*—P. Ponnaluri
(74) *Attorney, Agent, or Firm*—Medlen & Carroll, LLP

(57) ABSTRACT

The present invention provides compositions comprising colorimetric assay liposomes. The present invention also provides methods for producing colorimetric liposomes and calorimetric liposome assay systems. In preferred embodiments, these calorimetric liposome systems provide high levels of sensitivity through the use of dopant molecules. As these dopants allow the controlled destabilization of the liposome structure, upon exposure of the doped liposomes to analyte(s) of interest, the indicator color change is facilitated and more easily recognized.

21 Claims, 11 Drawing Sheets

(3 of 11 Drawing Sheet(s) Filed in Color)

OTHER PUBLICATIONS

Swalen et al., "Molecular Monolayers and Films," *Langmuir* 3:932–950 (1987).

Tieke, "Langmuir–Blodgett Membranes for Separation and Sensing," *Adv. Mat.* 3:532–541 (1991).

Whitesides et al., "Wet Chemical Approaches to the Characterization of Organic Surfaces: Self–Assembled Monolayers, Wetting, and the Physical–Organic Chemistry of the Solid–Liquid Interface," *Langmuir* 6:87–96 (1990).

Charych et al., "Specific Interaction of Influenza Virus with Organized Assemblies of Polydiacetylenes," *Mat. Res. Soc. Symp. Proc.* 282:153–161 (1993).

Charych et al., "Direct Colorimetric Detection of a Receptor–Ligand Interaction by a Polymerized Bilayer Assembly," *Science* 261:585–588 (1993).

Spevak, "The Presentation of Biological Ligands on the Surface of Polymerized Monolayers and Liposomes," Ph.D. Dissertation, University of California at Berkeley (1993).

Lio et al., "Atomic force microscope study of chromatic transitions in polydiacetylene thin films," *J. Vac. Sci. Technol.* 14(2):1481–1486 (1996).

Leung et al., "Imaging of polydiacetylene on graphite by scanning tunneling microscopy," *J. Appl. Phys.* 69(4):2044–2047 (1991).

Rieke et al., "Spatially Resolved Mineral Deposition on Patterned Self–Assembled Monolayers," *Langmuir* 10:619–622 (1994).

Dagani, "Lipids and Minerals Form Novel Composite Microstructures," *Chem. & Eng. News,* 19–20 (1993).

Kessel and Granick, "Formation and Characterization of a Highly Ordered and Well–Anchored Alkylsilane Monolayer on Mica by Self–Assembly," *Langmuir* 7: 532–538 (1991).

Miyasaka et al., "Oriented Polypeptide Monolayers by Rapid Spontaneous Condensation of Amphiphilic Amino Acid Esters," *The Solid Films* 210/211:393–396 (1992).

Perez et al., "Toward Inorganic Monolayers Inserted in a Langmuir–Blodgett Matrix," *Thin Solid Films* 210/211:410–411 (1992).

Tanev and Pinnavaia, "Biomimetic Templating of Porous Lamellar Silicas by Vesicular Surfactant Assemblies," *Science* 271:1267–1269 (1996).

Charych et al., "A 'litmus test' for molecular recognition using artificial membranes," *Chem. And Biol.* 3:113–120 (1996).

Pons et al., Biochimica et Biophysica Acta., vol.693., pp. 461–465., 1982.*

* cited by examiner

| FIG. 2A |
| FIG. 2B |

US 6,183,772 B1

DOPED COLORIMETRIC ASSAY LIPOSOMES

The present application is a continuation in part of prior-filed U.S. patent application Ser. No. 08/389,475 filed Feb. 13, 1995, now abandoned.

This invention was made with Government support under Contract No DE-AC03-76SF00098 between the U.S. Department of Energy and the University of California for the operation of Lawrence Berkeley Laboratory. The Government has certain rights in this invention.

BACKGROUND OF THE INVENTION

The present invention relates to an improved method for direct detection of analytes, where sensitivity of color changes in liposomes which occur in response to selective binding of analytes to their surface is improved by doping with promoter molecules.

CONVENTIONAL ASSAY METHODS

Analytical Chemistry Analytical chemistry techniques have been used for many years to determine such medical parameters as hematocrit levels. While useful in their own right, analytical chemistry methods are of limited or no practical applicability to many biological systems in which assessment would be valuable. Unless expensive and cumbersome gas chromatography methods are used, large quantities of analytes are generally required to accomplish such methods. Often, quantitative results are limited or not available. However, such techniques are used for such basic chemical tests as creatinine assays.

Microbiology and Pathology Methods Another approach to medical-biological systems analysis has been direct microscopic observation using various cell-staining and classic pathology techniques. Augmenting these capabilities have been well developed microbiological techniques, such as culturing, colony characterization, and observation of metabolic and nutrient limitations. Most of medical science have been developed using this basic arsenal of analytic techniques. While culturing and direct tissue observation techniques have served as the bulwark of medical detection processes for many years, they have important limitations.

Pathological analysis of patient tissues to determine the development of a disease state and the identification of the causative pathogen generally requires an invasive procedure. Culturing a pathogen from various body fluid or other samples is typically time consuming and expensive.

Immunoassays A breakthrough in medicine occurred with the development of immunoassay techniques. In these methods, an antibody is developed which will specifically bind to a target of interest. While costly in both their development and production, antibodies from animals allowed a very accurate analysis of a number of analytes which had previously been virtually unassessable in both research and particularly clinical situations.

An important technical advancement in immunoassay was the development of monoclonal antibodies. Instead of exposing an animal to an analyte and harvesting its full range of antibodies, in this technique a single spleen cell of a sensitized animal is rendered immortal and cloned, providing multiple identical copies. The resulting cell line is then cultured to produce a very specific and pure antibody product.

In immunoassay systems the antibody can be labeled in some way so that the binding event can be detected. This can be done with a dye, fluorescent, radioactive or other label. Conversely, if binding inhibition occurs between a known amount of introduced, labeled analyte and the material to be analyzed, the diminution of the signal will indicate the presence of test analyte. If the agglutination of the antibody particles is of sufficient volume and density, the formation of a precipitant can also serve to signal the presence of an analyte.

In recent years, the research and medical communities have come to rely heavily on immunoassay techniques to detect and quantify biological materials. While successful in many respects, the indirect nature of immunoassay methods as well as their dependence on antibody materials results in a variety of complications, problems, and assay limitations. The development and production of antibodies remain expensive, and these molecules are sensitive to environmental changes. Also, only those materials to which antibodies can be produced can be detected by these systems.

LANGMUIR-BLODGETT FILM ASSAYS

The techniques of molecular self-assembly, such as that described by Swalen et al., (*Lanqmuir*, vol. 3, page 932, 1987) as well as Langmuir-Blodgett (LB) deposition (Roberts, Ed. *Lanqmuir-Blodqett Films*, Wiley, New York, 1966) have been used for coating surfaces with a well-defined, quasi two-dimensional array of molecules. The initial use for this new advancement was for materials science applications such as wetting (Whitesides, et al., *Lanqmuir*, vol. 6, p. 87, 1990) and friction (Novotny et al., *Lanqmuir* vol. 5, p. 485, 1989).

These bilayer films are also used as immobilizing supports for analytic reactions. Biosensors based on LB films can detect molecules of diagnostic significance such as glucose (Okahata, et al., *Thin Solid Films*, vol. 180, p. 65, 1989) and urea (Arisawa, et al., *Thin Solid Films*, vol. 210, p. 443, 1992). In these cases, classic analytical chemistry systems are immobilized on the films in order to improve the readout of the test results and otherwise simplify and improve the detection capabilities of the test procedure.

The detection of receptor-ligand interaction is generally accomplished by indirect assays such as the enzyme-linked immunosorbent and radio-labeled ligand assay. Although biotechnological functionalized films have led to elegant examples of molecular recognition at an interface, the problem of transducing the molecule recognition event into a measurable signal has remained a difficulty until the advent of the subject invention.

In the case of biosensor devices, detection is generally carried out by coupling the LB films to a secondary device such as an optical fiber (Beswick, *Journal Colloid Interface Science*, vol. 124, p. 146, 1988), quartz oscillator (Furuki et al., *Thin Solid Films*. vol. 210, p. 471, 1992), or electrode surfaces (Miyasaka, et al., *Chemical Letters*, p.627, 1990).

Some of the analyte bound films provide for fluorescent label, where the fluorescence or its quenched state indicate the occurrence of a binding event (Beswick, *Journal Colloid Interface Science*, vol. 124, p. 146, 1988). In some cases, these detection materials have been embedded in the surface of the supporting bi-lipid layer (Tieke, *Advanced Materials*. vol. 3, p. 532, 1991).

Polydiacetylene films are known to change color from blue to red with an increase in temperature or changes in pH due to conformational changes in the conjugated backbone (Mino, et al., *Lanqmuir*, vol. 8, p. 594, 1992; Chance, et al., *Journal of Chemistry and Physics*, vol. 71, p. 206, 1979; Shibutag, *Thin Solid Films*, vol. 179, p. 433, 1989; Kaneko, et al., *Thin Solid Films*, vol. 210, p. 548, 1992).

FUNCTIONALIZED LIPOSOMES

Unpolymerized liposomes expressing sialic acid residues have been extensively used as model systems to study the interaction between influenza virus and cell surfaces (Ott, et al., *European Journal of Pharmacological Science*, vol. 6, p 333, 1994). These liposomes are typically made of such lipid materials as cholesterol and egg phosphatidylcholine (Kingery-Wood, et al, *Journal of the American Chemical Society*, vol. 114, p 7303, 1992).

A therapeutic functionalized liposome which is produced through polymerization was developed by some of the inventors (Spevak et al, *JACS*, p 115, 1993). The standard in the field is to progress with the polymerization procedure until the materials are fully red, indicating that the polymerization is complete. This was the procedure used in the above cited publication.

While it has been a goal of the research community to exploit this characteristic in the detection of binding events, researchers have yet to develop a method using this phenomenon in practical applications.

GENERAL DESCRIPTION OF THE INVENTION

The present invention allows direct detection of protein toxin by the observation of color changes which occur when these analytes bind to the inventive doped calorimetric liposomes. Using promoter molecules to dope calorimetric assay liposomes this inventive technological advancement provides a dramatic intensity of indicator at low levels of analyte allowing unprecedented sensitivity and improved quantitation. Additionally, the present invention enjoys the many advantages which accrue when a test system can be suspended in fluid.

It is an object of the present invention to assay the presence of biomolecules by directly detecting the binding event when the analytes specifically bind to colorimetric liposomes optimized by doping with promoter molecules.

It is a further object of the present invention to provide for the direct detection of viruses, bacteria, parasites, and other pathogens, and drugs, hormones, cell wall fragments, membrane fragments, membrane receptors, enzymes, and other biologically relevant materials using the inventive assay system.

The present inventive assay means and method provide for the direct calorimetric detection of a receptor-ligand interaction using novel doped calorimetric liposomes. Using the inventive method of producing these original doped calorimetric liposomes, a ligand or its derivative is rendered polymeric by polymeric linking of the ligands through a linking arm, or through direct incorporation during the polymerization process. Some of these aspects of the present invention are described in the inventors' recently published communication, incorporated by reference herein, (Reichert et al, *J. Am Chem. Soc.*, vol. 117, p 829, 1995).

The presence of an analyte which binds to the incorporated ligands can be detected by observing changes in the spectral characteristics of the polymeric assemblies. The polymer-ligand assembly thus encompasses a molecular recognition site and a detection site, all within a single molecular assembly.

In one embodiment of the invention, doped chromatic polydiacetylene liposomes are produced, and placed in a liquid. The test sample is added. The color change which occurs indicates the presence of the analyte, and the intensity and degree of the color allow a quantification of the concentration.

The inventors have prepared synthetic, polymerizable liposomes that resemble the organization and functionalization of cell membranes and have employed them as simple calorimetric sensors. In one embodiment of the invention, the liposomes were designed to specifically bind to influenza virus particles and protein toxins and, in addition, report the binding event by undergoing a visible color change. In effect, these molecular assemblies mimic cell surface molecular recognition as well as signal transduction.

In order to impart both molecular recognition and detection functions to the liposomes, the inventors combined a known ligand—receptor interaction with the unique optical properties of polydiacetylenes. The conjugated backbone of alternating double and triple bonds gives rise to intense absorptions in the visible spectrum. In single crystals or Langmuir-Blodgett films, these materials are known to undergo blue to red color transitions due to a variety of environmental perturbations including heat, mechanical stress, pH, and solvent.

Two different approaches can be used to functionalize the surface of the assembly. In one case, the diacetylenic monomer lipid is directly derivatized with the appropriate binding ligand by synthetic coupling. This allows direct cross-linking of the "ligand-lipid" with the surrounding polydiacetylene "matrix". Binding affinity can be controlled by suitable modification of ligand structure. Alternatively, a specific receptor molecule can be non-covalently incorporated into the polydiacetylene matrix in a manner analogous to the heterogeneous mixture of molecules in cell membranes.

Direct Derivatization

In one embodiment of the subject invention, the inventors have demonstrated that specific binding of influenza virus to functionalized polydiacetylene liposomes produces an analogous color transition. Influenza virus particles were enveloped by a lipid bilayer to which the hemagglutinin (HA) lectin is anchored. HA binds to terminal alpha glycosides of sialic acid on cell-surface glyco-proteins and glycolipids, initiating cell infection by the virus. As described in the prior art section of the subject application, liposomes expressing sialic acid residues have been extensively used as model systems to study the interaction between influenza virus and cell surfaces. The polymerized liposomes of the subject invention, however, are composed of molecules that allow direct visualization of this specific interaction.

This is an example of a wholly synthetic cell membrane-like structure. In this case, the C-glycoside of the carbohydrate sialic acid has been covalently coupled to 10,12-pentacosadiynoic acid, followed by cross-linking of the ligand to a 'matrix' lipid. Influenza virus binds to this assembly by the viral hemagglutinin (HA) lectin. HA binds to terminal $\alpha$-glycosides of sialic acid on cell-surface and glycolipids initiating cell infection by the virus.

Specific, desirable properties can be built into the ligand-lipid molecule to enhance binding and stability. For example, the bifunctional sialic acid derivatized PDA incorporates both the sialic acid ligand for viral binding and the diacetylenic functionality in the hydrocarbon chain for polymerization. The carbon-glycoside in this compound was designed into the structure to prevent hydrolysis by viral neuraminidase. The derivatized PDA can be mixed with 10,12-pentacosadiynoic acid and formed into thin films or liposomes. Optimal sialic acid derivatized PDA sensors are composed of 5–10% sialic acid lipid and 90–95% matrix lipid.

Non-Covalent Incorporation

If the ligand of interest resides at the biological cell surface, it can be directly incorporated into the macromolecular assembly, avoiding potentially complex synthetic steps. A suitable system to demonstrate functionality for such an approach is the family of gangliosides that reside on the cell surface of neurons. Gangliosides are lipid molecules that are located in the plasma membrane of cells and have a carbohydrate recognition group attached to the extracellular surface. The lipid anchors the carbohydrate into the cell membrane, providing the biological basis for allowing incorporation of gangliosides into the artificial PDA assemblies or liposomes.

In one embodiment of the subject invention, two representative members of this family are the $G_{T1b}$ and $G_{M1}$ gangliosides (FIG. 2B, compounds 4,5). The $G_{m1}$ ganglio- sides located in intestinal cells, are the primary target of cholera toxin, the neurotoxin responsible for the disease cholera (Cuatrecasas, *Biochemistry*, p. 3547, vol. 12, 1973). The $G_{T1b}$ gangliosides located at the neuromuscular junction are the primary target of botulinum neurotoxin, the neurotoxin responsible for botulism (Ledeen, *Gangliosides*, 1982). The chromatic unit of the neurotoxin sensor is composed of PDA and 'promoter' PDA.

It is a theory of the present inventors that the addition of 'promoter' PDA lowers the activation barrier of the chromatic transition or provides a connection between the non-conjugated receptor and the conjugated backbone, enabling the neurotoxin to induce the calorimetric transition. The promoter lipid used in these investigations is the sialic acid or lactose derivatized PDA lipid (FIG. 2A, compounds 2, 3).

It should be noted that in this case, the derivatized lipid is used to modify the film's optical properties and not as a molecular recognition site as in the case of influenza virus detection. The polydiacetylene bio-assembly containing only sialic acid derivatized PDA or lactose derivatized PDA does not respond to the neurotoxins used in this study, indicating that there is no sufficient interaction between the neurotoxins and the derivatized diacetylene lipid to induce the color change. It is a theory of the inventors that the sialic acid may not be physically available for binding because of the longer ligand protruding from the surface of the liposomes.

Advantages of the Invention

General Advantages of the Invention The subject invention represents a dramatic advancement over both prior art direct chemical and immunoassay systems, achieving advantages which, prior to the present invention, were available exclusively in only one or the other of these analytic art methods. Much as the advent of immunoassay techniques revolutionized medical and research analytical capacities, the subject invention represents a critical advancement in the analytical arts.

The present invention allows the advantages of both immunoassay and chemical analysis in a single system. The inventive calorimetric liposome assay enjoys the direct assay advantages of analytical chemistry methods, with many of the advantages inherent in such systems. The inventive assay technique also has a substantial environmental range of testing beyond that of immunoassays. This allows the accommodation of various analytes in their most advantageous environmental parameters. Additionally, the present invention allows rigorous, direct analysis to occur even in very narrow environmental ranges, previously unavailable with analytical chemistry techniques. The speed and simplicity of the color change indicator of the subject invention are its hallmark advantages.

Qualities of Analytical Chemistry Analytical chemistry techniques are the only assay system prior to the advent of the subject invention that allowed direct detection of an analyte. Analytical chemistry techniques have been used for the accurate quantitative of such biologically and medically critical analytes as hematocrit and creatinine.

Prior to the present invention, analytical chemistry methods were virtually unavailable for most biological molecules due to the destruction of the analytes' characteristics during preparation and analysis steps, and the typically small amount of the analyte present in the test sample.

Analytical chemistry has limited applicability to many biological system's assay needs. Unless expensive and cumbersome gas chromatography methods are used, large quantities of analyte are required. Often, quantitative results from such methods are limited or not available. Thus, the advent of immunoassay techniques were revolutionary in the biological sciences.

Qualities of Immunoassays Immunoassays have been heavily relied upon by both researchers and clinicians to assay most biological molecules. The present invention shares with immunoassay techniques the ability to assay biological materials in conditions close to normal biological parameters such as temperature, pH, salinity, etc. Most biological molecules are notoriously difficult to assay using direct analytical chemistry techniques due to the severe limitation of environmental ranges which these analytes can tolerate without losing their specific characteristics.

While successful in many respects, the indirect nature of immunoassay methods overcome by the present invention previously resulted in a variety of interferences, complications, problems, and assay limitations. The requirement that an antibody be developed and produced for each possible target limits the efficacy of immunoassay methods in such applications as designer drug development and screening. Ironically, while allowing testing within a portion of biological environmental ranges, the large glycoproteinaceous antibodies are often highly sensitive to degradation outside of a small testing parameter environmental range. Thus, the susceptibilities of antibodies to environmental rigors in field testing situations limit the environmental testing range available in these assay systems.

A subtle disadvantage to immunoassay systems which has also been overcome by the subject invention occurs in rapidly evolving pathogens such as the influenza virus. In such organisms, especially in the case of viruses, the external coat which is available for immune reactions constantly shifts its antibody recognition elements. Thus, despite a full blown immunity response to an influenza strain, within months an individual can again develop flu, but from a pathogen with an external coat so modified that it is immunologically unrecognizable by the victims' memory cells. This is the reason individuals can develop flu year after year.

Unique Qualities of Doped Colorimetric Liposomes While maintaining the advantages of immunoassay and analytical chemistry techniques, the present invention enjoys the unique advantage of being able to directly detect biological analytes. This advantage of the present invention represents a revolutionary advancement in the biological assay field. Combining the direct, quantitative detection methods of analytical chemistry with the biospecificity and mild testing conditions of immunoassays provides a uniquely powerful tool for researchers and clinicians alike.

Avoiding the need for use of immunoglobulins to provide biospecificity is a very important advantage of the present invention. In contrast to assays requiring binding to immunoglobulins, in one embodiment of the present invention, the host attachment site on the pathogen is exploited for its recognition function. This site, generally in an immunologically inaccessible valley on the pathogen surface, is highly genetically conserved over time. The minimal variability of an attachment site is necessary for the pathogen to maintain its infectivity. As a result, a single assay system of the present invention will provide effective assays for a panoply of influenza strains, many of which may be very newly evolved.

There are many advantages to the genetically conserved host recognition site being targeted by the embodiment of the present invention. A determination of a patient's exposure to the virus or toxin will be definitive, and not limited to a particular strain. This advantage of the present invention also avoids the need for a large number of immunological tests, as the clinician can rely on a single assay. Additionally, even newly evolved, uncharacterized flu strains can be identified, further avoiding false negative tests.

An analogous limitation of immunoassays occurs in well established pathogens such as malaria parasites. In these organisms, phases of the life cycle which would allow for an immune response have over time been so limited as to avoid the immune response, or have been made to occur within host cells so as to avoid an antibody reaction.

The present invention exploits the genetically conservative host binding site to identify the pathogen. Even in comparatively large parasites, the host binding site tends to be held constant over time throughout the generations of pathogens. Additionally, parasites are usually present in the body in a large number of diverse life stages. In well established parasites, the immune accessible sites often vary considerably from stage to stage, the advantage being that the host organism is unable to mount a immunological response with sufficient rapidity to avoid the entrenchment of the parasite.

Dopant Materials

A large variety of materials are used as dopants in the subject invention. Materials from 30 MW to 2,500 MW can be effectively utilized to imbue increased sensitivity to the inventive liposomes. A preferred range for these materials is from 100 MW to 1,000 MW. A most preferred weight for the dopant materials is 100 MW.

A dopant "cocktail" will in many cases allows an optimal, customized liposome for a particular analytic system. Mixing various dopants for use in a system can provide excellent results. For instance, the inventors have provided a dopant cocktail which is a mix of glucose and polydiacetylene. The glucose component of the dopant mixture appears to act primarily to prevent non-specific adhesion to the surface of the inventive liposome and may also enhance sensitivity. The polydiacetylene bound sialic acid component appears to functionally destabilize the surface to provide a dramatic increase in sensitivity. By using this co-dopant approach, both specificity of adhesion and sensitivity are optimized, without unduly compromising the structural integrity of the inventive liposome.

In one preferred embodiment of the present invention, a dopant constituent can be a diacetylene lipid with a charged head group. The head group can be chosen at a larger size commensurate with the size of the target analyte. Similarly, when there is a longer chain length, the dopant head group can be of a larger size.

While one would generally select the size of the head group of a diacetylene, dopant constituent to be proportionate to the size of the target analyte or or the same size as the ligand, there is also the opportunity to provide useful steric hindrance. For instance, a larger head group on the dopant may demand very specific, rigorous binding of analyte in order to overcome steric hindrance to analyte binding provided by the dopant. This would assure that non-specific binding would be limited or precluded. This approach represents an opportunity to improve the specificity of the inventive analytic system.

Materials of a variety of chemical makeups are useful as dopants in the present invention. In one embodiment, diacetylene lipids with charged head groups are useful, such as those described in the example section. Polyethylene glycol, such as those used in stealth liposome technology and others used for preventing immunoresponse and non-specific adsorption are also very appropriate to the present invention (Lasic et al., *Stealth Liposomes* CRC Press, Boca Raton, Fla. 1995).

Materials which are incorporated into cell membrane structures in nature are generally useful as dopants in the present invention. For instance, the various cholesterols represent potential dopants that can provide useful degrees of destabilization or stabilization to the subject lipid structure.

Surfactant type compounds also serve in a doping function, although they may not always be incorporated into the final structure. For example, the detergent TWEEN 20 has been shown by the inventors to produce a very dramatic intensity to the blue color of the liposomes of certain embodiments of the present invention.

An alternative surfactant that can be used are peptidedetergents, small amphipathic molecules that have a hydrophobia region mimicking the membrane spanning regions of membrane proteins. These small peptides (typically 20–25 amino acids in length) can be incorporated into the liposomes to alter the stability or sensitivity of the calorimetric response of the material when exposed to specific analytes. Since peptide-detergents are bulkier in the hydrophobic region of the material, they are able to have a more pronounced effect on film stability or sensitivity than other surfactant molecules.

Lipids from natural sources are also useful as dopants in the present invention. Excellent sources for these lipids are various yeast species, and also plant sources, such as soybeans.

Percentages of Dopants

The most appropriate percentage of dopant incorporated into the structure of the inventive liposomes is dependent on the particular analytic system being developed, and the needs of the testing situation. For instance, sensitivity may be compromised to some extent in favor of long shelf life, or to accommodate rigorous field conditions. The percentage of dopant in the inventive system is theoretically limited only to that which will not preclude sufficient incorporation of the indicator polydiacetylene molecules to produce the necessary optical density and color change.

Percentages of dopant can vary from as low as 0.01%, where increases of sensitivity have actually been observed by the inventors, to 75%, after which the structural integrity of the liposomes typically begins to suffer. A preferred range for dopant is 2%–10%. In certain embodiments of the present invention, the optimal percentage of dopant is about 5%. The relative appropriate percentages of dopant materials in a dopant cocktail will allow flexibility in total percentage of dopant to the polydiacetylene indicator.

Dopant Incorporation Parameters

In selecting appropriate incorporation methods for the dopant, there are several competing considerations. In the sonication bath method, the incorporation is very controlled, and requires several hours of processing. This relatively slow, gentle incorporation method allows the incorporation of comparatively large or complex dopant materials. However, the sonication bath approach is only suitable when a relatively low percentage of dopant is to be incorporated.

The point probe method allows the incorporation of a much higher percentage of dopant material over a shorter period of time, t ypically from one to ten minutes. However, this method is typically limited to incorporation of small to intermediate sized dopant materials.

The temperatures chosen for incorporation are selected based on the particular analytical system and liposome parameters desired. The temperatures can range for 46° C. to 55° C. In the bath system, the range is generally from 10° C. to 30° C. The sonication point generally is accomplished at about 20° C. The temperature can be varied throughout a run to optimize results, for instance lowering the temperature to stabilize the system towards the end of the run, prior to a possible structural compromise of a large dopant material.

Parameters such as pH and choice of dilutents can be selected for each particular systems optimally as is obvious to the practitioner. The blue form of the liposomes tends to be more unstable at high pH (greater than 8.0).

Target Materials

One of the unique advantages of the subject invention is the wide range of target materials, binding events, and biochemical reactions amenable to analysis using the inventive techniques. Many of these materials previously could not be detected using a straightforward, practical assay. The present invention allows many advantages of immunoassay systems, without the complications of immunoglobulin generation or indirect analysis.

In general, the present invention requires no pre-analysis purification step. This feature of the subject invention is due to the high specificity of the ligands incorporated into the detecting doped colorimetric liposomes. Additionally, the inventive direct assay system avoids the expense, complications, and increased inaccuracies inherent in the indirect systems currently available.

Sensitive Analvtes-Gentle Testing Conditions The inventive doped calorimetric liposomes can employ ligands and analytes which are stable or enjoy appropriate binding characteristics in a limited in vitro or environmental range of conditions. Within in vitro range conditions, the present invention is useful in that stringent limitations even within this narrow range of conditions can be met. This allows, for instance, three dimensional conformations of sensitive biochemicals and biomolecules to be maintained throughout the testing procedure.

The present invention functions well even in carefully limited conditions. Thus, conditions such as pH, saline, and temperature can be carefully controlled by feedback controls, titration and other techniques without interfering with the accuracy or sensitivity of the analysis.

Because of this wide experimental range advantage of the present invention, intact cells or sensitive subcellular inclusions can be assayed without disturbing their structural integrity. The color change when the inventive doped liposomes bind to a surface will pinpoint the location of an analyte, such as in a tissue sample.

Subtle cellular development stages can be monitored by the present invention, such as the various stages of malaria infection. Additionally, the association between various factors can be tested or monitored even during the interaction process using the method of the subject invention.

Weak Binding Analytes-Multivalency The multivalent feature of the polymer-linked or directly incorporated ligands of the subject invention provide a heightened binding capacity in the case of naturally multivalent analytes. Multivalency can also be provided for limited valency analytes prior to the test procedure to imbue them with this advantage of the subject invention. The inventive exploitation of multivalency allows a specific but weak interaction to be amplified many fold.

A structural linker of sufficient length and conformability can aid in allowing binding of multiple sites on the analyte even when they are conformationally separated on a curved surface. As a result of these special features, the present invention can detect many ligands previously unsuitable for assay evaluation.

The main criteria for effective indication of the presence of analyte is that the surface of the doped calorimetric liposomes be sufficiently perturbed to produce the requisite spectral change. Binding the analyte to an immobilizing particle will in some embodiments of the present invention serve this purpose, as it concentrates the analyte in a small area, and further provides a three-dimensional aspect over a relatively large area to even a small analyte.

A large variety of ligands can be employed in the subject invention, allowing great flexibility in detecting a multivalent test target. Ligand selection can be based on the most advantageous binding and steric characteristics, rather than compromising these factors to accommodate the test system. Thus, the most advantageous ligand can be selected based on such factors as hydrophobicity and hydrophilicity, size, position of binding site, and conflicting affinities. Ligands which can be employed in the subject invention can include ligands which occur naturally in cellular membranes and can be utilized without resort to a structural linker or molecular synthesis.

Challenging Analytes The rigor and outstanding advantages of the inventive doped colorimetric liposomes allow the detection and quantitative evaluation of materials which have been previously unachievable because of the limitations of the prior art methods.

The inventive liposomes and assay method can detect and quantify very small biological or other molecules for which antibodies can not be developed such as protein or bacterial toxins. This is particularly true where a ligand which is normally a part of a cell membrane is utilized.

Signal Observation

Various spectral changes to the bi-layer can be used to detect the presence or absence of the target material. Means of amplifying the spectral signal well known in the art can also be employed when low levels of analyte are present. Because of the empirical nature of the signal, there are many opportunities for automating the read out of the present inventive assay system.

In one particular embodiment of the present invention, a blue to pink color shift can be observed simply by visual observation by the testing technician. Because of the simplicity of the observation, this function can easily be accomplished by an untrained observer such as an at-home user. Alternatively, spectral test equipment well known in the art can be employed to determine a change in spectral qualities beyond the limits of simple visual observation, including optical density to a particular illuminating light wavelength.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIG. 4b is a graph showing the change in UV-VIS absorption spectra as in FIG. 4a.

FIG. 5b is a graph of changes in the visible absorption spectra as per FIG. 5a.

DETAILED DESCRIPTION OF THE INVENTION

The inventive doped colorimetric assay liposomes allow for the direct detection of the presence of a wide range of analytes by changes in color. The results can be read by an untrained observer, and the test can be conducted in ambient conditions. Very mild testing conditions are possible, which allow the detection of small biomolecules in a near natural state, providing information as to their interactions and avoiding the risk of modification or degradation of the analyte.

The inventive doped colorimetric liposomes are composed of a three-dimensional structure. This can be in the form of a classic liposome, a tubule or other structure whose surface contains both orienting and detecting head groups. The detecting head groups are composed of a ligand specific to the analyte in question, which is bound to one terminal end of a linear structural linker. This linker, in turn, is bound to the doped liposome by its second terminal end. The doped liposome surface is also provided with lipid ordering head groups.

Figure 1A:
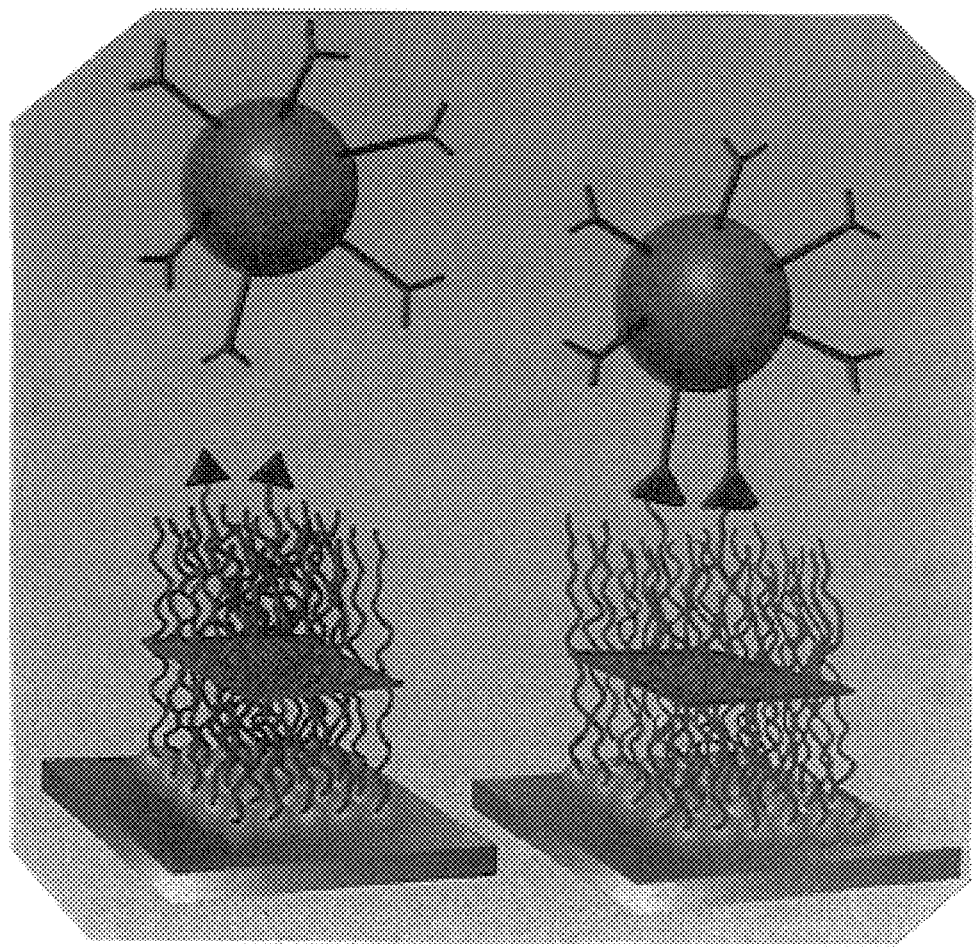
FIG. 1a is a schematic view of the construction of calorimetric biosensors.
Figure 1B:
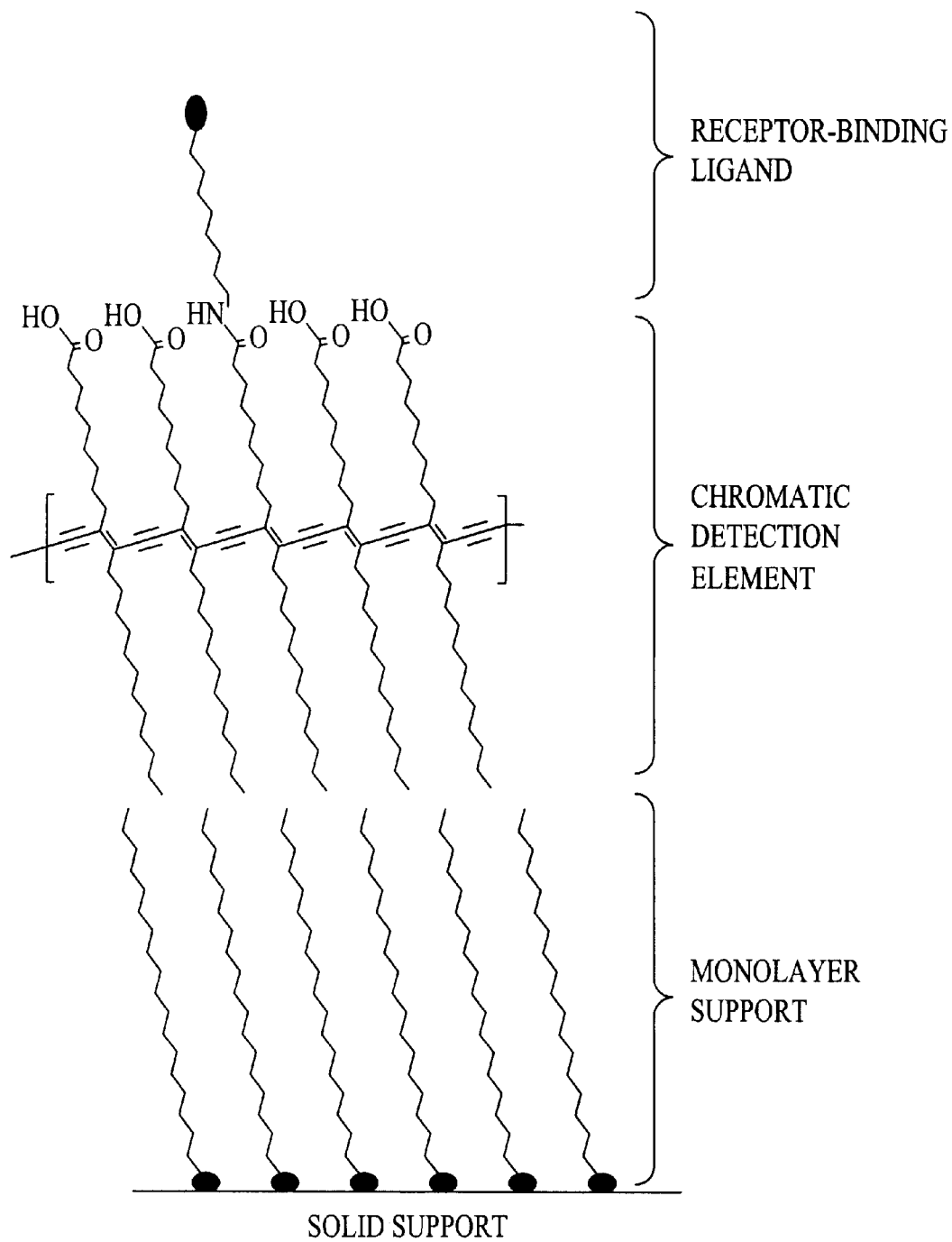
FIG. 1b is a schematic representation of polydiacetylane thin films on a solid support.
Figure 1C:
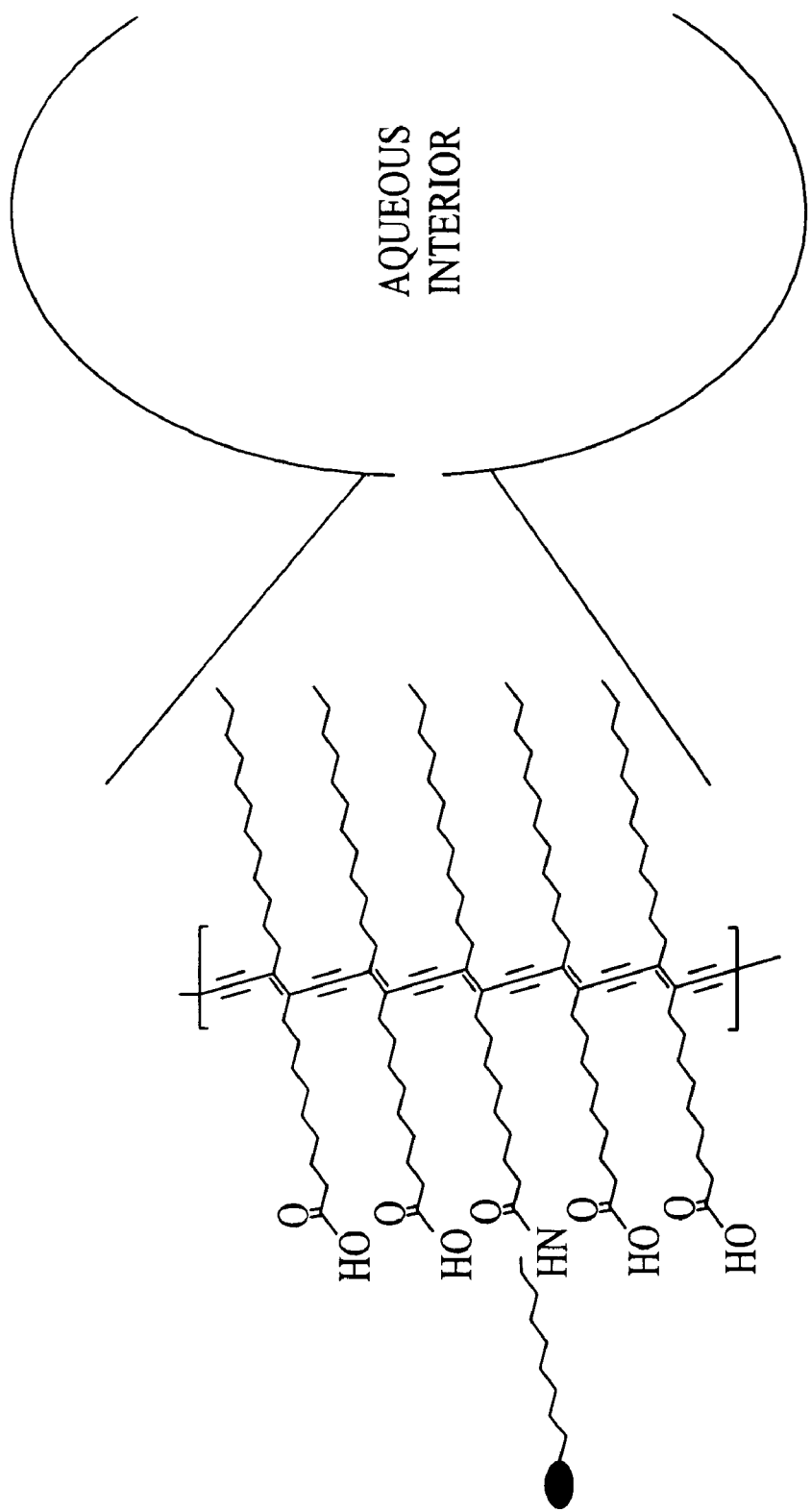
FIG. 1c is a schematic representation of polydiacetylene calorimetric liposomes.

FIG. 1 provides a schematic view of the mechanisms involved in making a calorimetric biosensor. FIG. 1a illustrates the engineered conjugated polymers before (left, blue) and after (right, red) exposure to a multivalent analyte. Binding to a molecular recognition site induces stresses that are detected by an optical 'reporter' element, which signal the binding event by changes in the optical absorption spectrum of the polymer. The two molecular architectures shown are FIG. 1b polydiacetylene thin films on solid supports and FIG. 1c polydiacetylene liposomes.

Lipid Orderina Groups The lipids appear to be important in structurally ordering the doped liposomes so that binding of the analyte produces a detectable color change.

Figures 2, 2A:
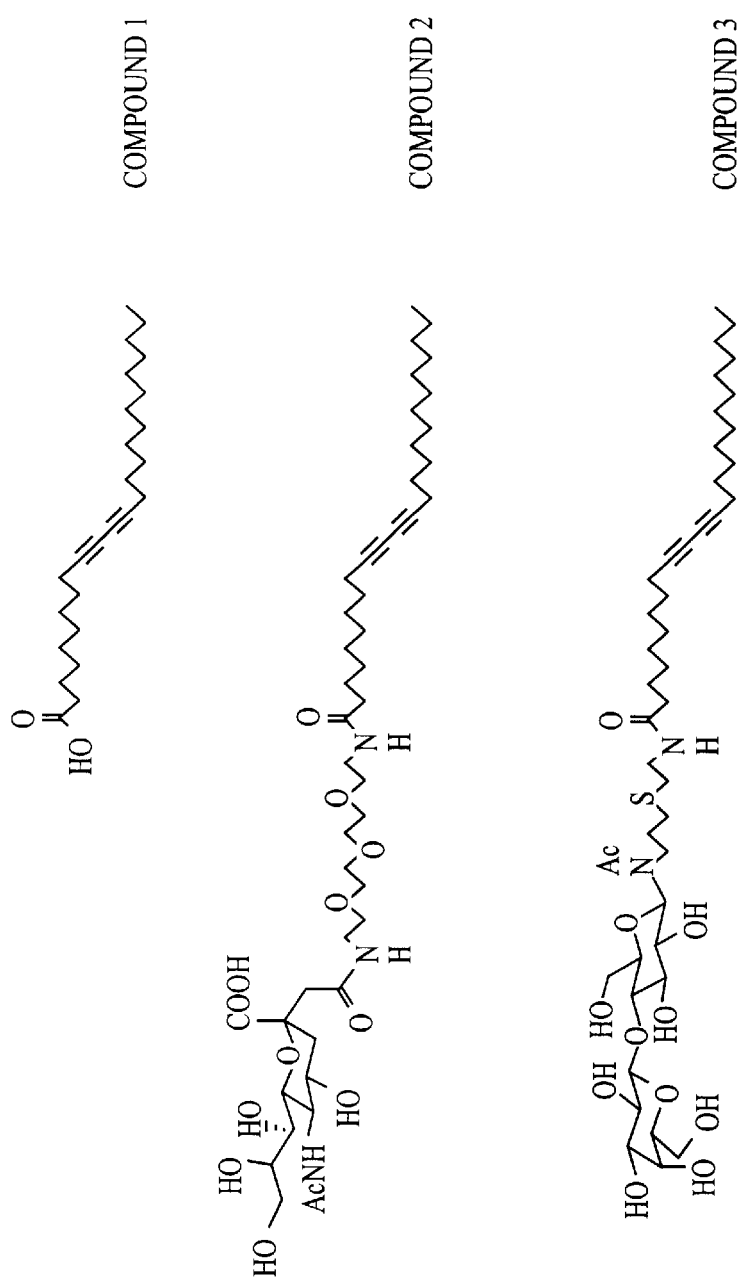
FIGS. 2A and 2B show the chemical structure of various components of the subject invention.
Figure 2B:
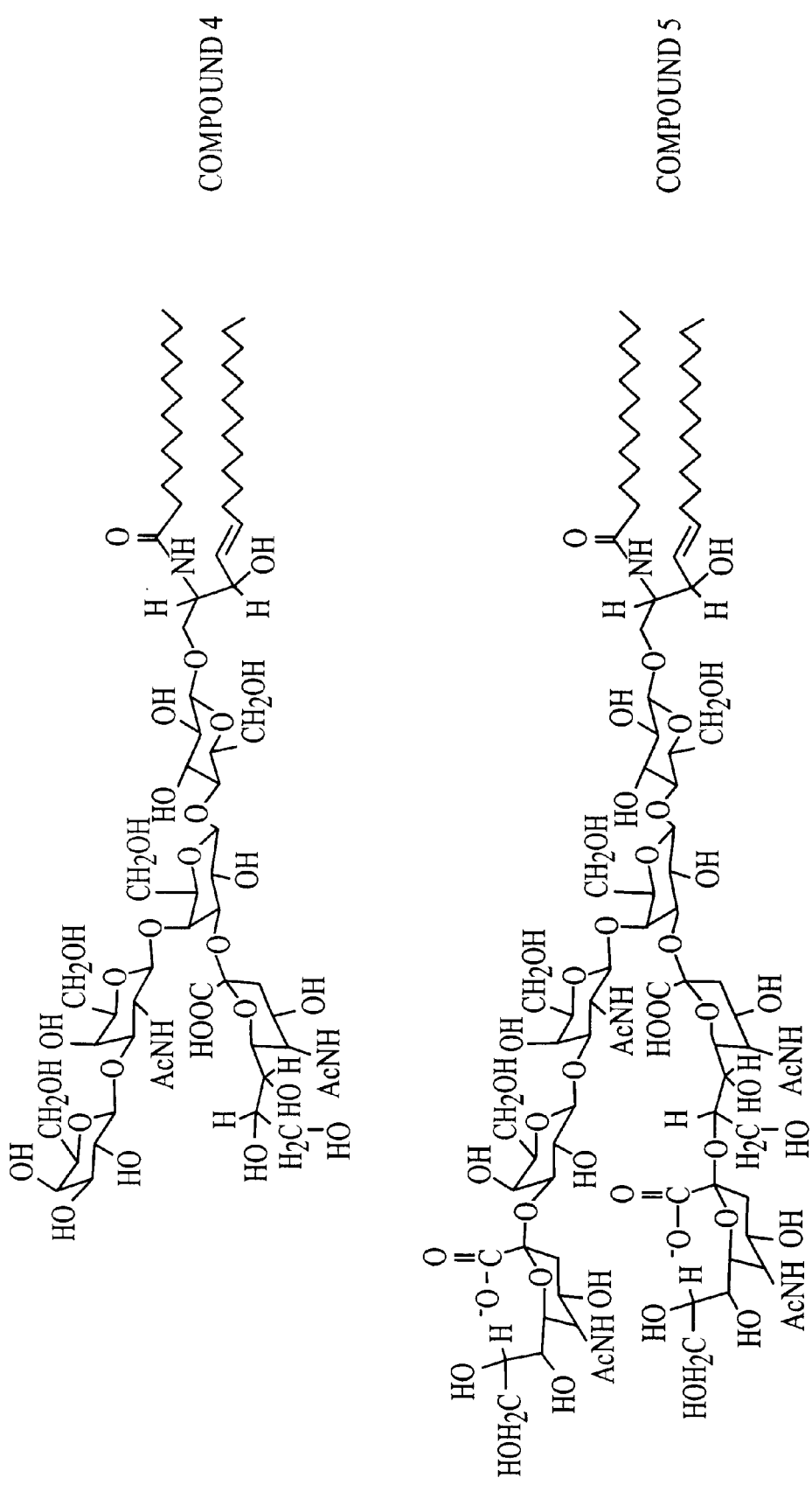
Figure 3:
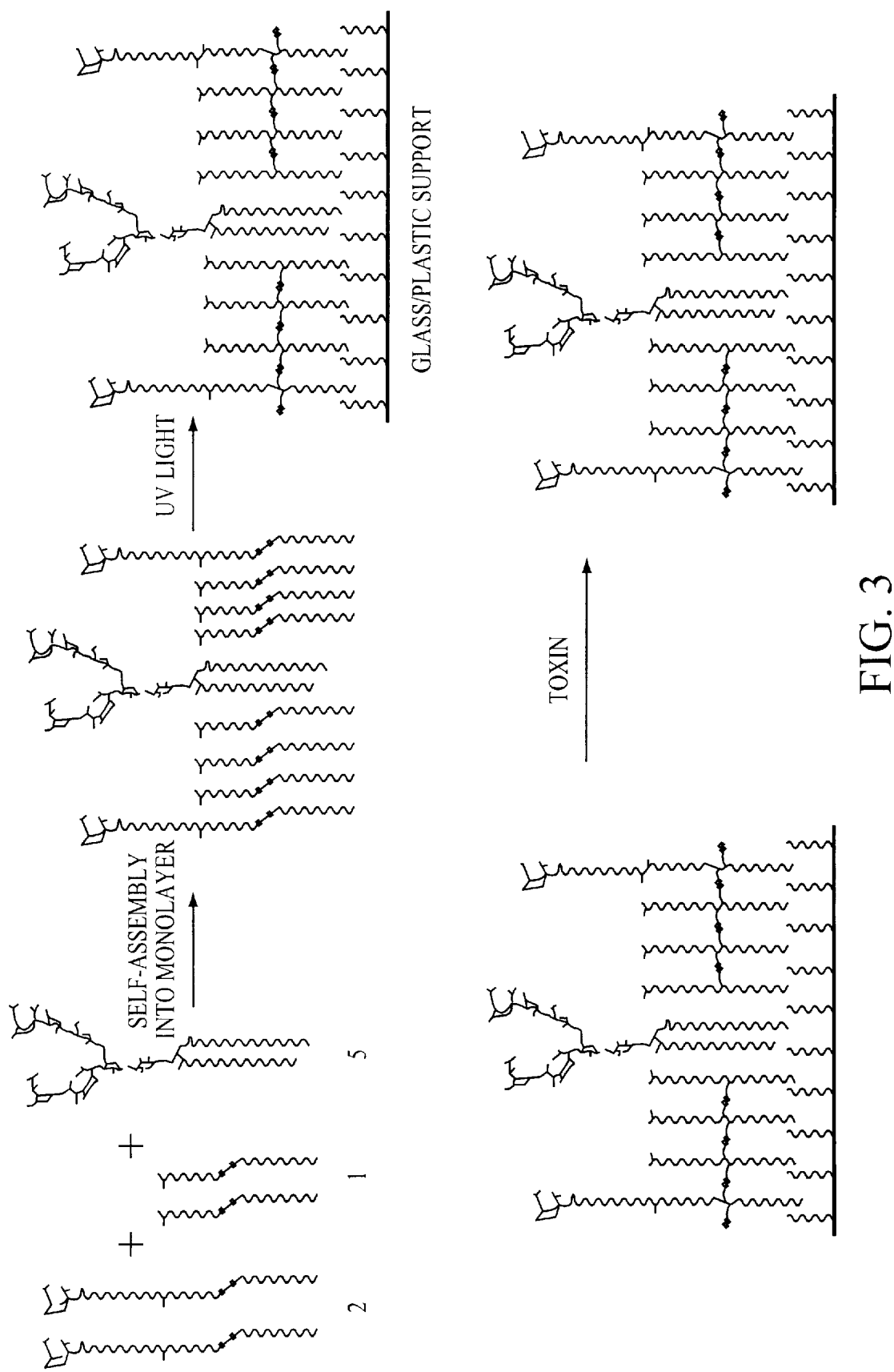
FIG. 3 is a flow chart showing the construction of doped thin film assemblies for toxin detection.

FIGS. 2A and 2B provide the lipids and lipid-linked cell-surface moieties used in the design of colorimetric sensors of biological ligands. Compound 1 is the matrix lipid 10,12-pentacosadiynoic acid (PDA), PDA derivatized with sialic acid (compound 2) is used as a binding site for influenza virus hemagglutinin or as a 'promoter' lipid for toxin-binding studies; lactose-derivatized PDA (compound 3) is also used as a dopant lipid in assemblies incorporating the ganglioside $G_{M1}$ (compound 4) and $G_{T1b}$ (compound 5). The gangliosides occur naturally in cell membranes, and are composed of a carbohydrate head group used in molecular recognition, and a ceramide lipid chain that resides within the cell membrane.

Applicants hypothesize that a structuring effect of the ordering groups serves to appropriately stabilize the physical structure of the doped calorimetric liposomes to facilitate color stability and polymerization. In turn, the binding of the analyte to the molecular recognition ligand groups then causes sufficient steric perturbation or stress of the structure to result in a color change. It may be that the stability and relative rigidity engendered by the ordering lipids unite the bilayer surface, so that a steric change in one area triggers a larger effect in the surface of the doped liposomes as a whole.

It is not certain which of the many effects of binding result in the observed spectral changes. The changes are due to stresses induced by binding which changes the effective conjugation length of the polymer backbone. The inventive three-dimensional structures are highly color sensitive to a number of environmental parameters, such as heat, and these factors may be a component of the observed phenomena as well.

However, the applicants are not bound to any of the above hypothesis which are simply attempts to explain the demonstrated effective assay method of the subject invention.

Previous studies have suggested that color transitions in polydiacetylenes arise from changes in the effective conjugation length of the polydiacetylene backbone and that the electronic structure of the polymer backbone is strongly coupled to side chain conformation. The inventors can only speculate at this point that specific analyte-liposome interactions may serve to alter side chain conformation, reducing the effective conjugation length of the polymer backbone. Indeed, theoretical calculations suggest that very slight rotations around the C—C bond of the polymer backbone decrease the π electron delocalization.

Materials for use are as head groups in the present invention include among others —$CH_2OH$, —$CH_2OCONHPh$—$CH_2OCONHEt$, —$CH_2CH(Et)OCONHPh$, —$(CH_2)_9OH$, —$CH_2OCOPh$, —$CH_2OCONHMe$, —$CH_2OTs$, —$CH(OH)Me$, —$CH_2OCOR_2$, wherein $R_2$ is a derivative of n-$C_5H_{11}$, n-$C_7H_{15}$, n-$C_9H_{19}$, n-$C_{11}H_{23}$, n-$C_{13}H_{27}$, n-$C_{15}H_{31}$, n-$C_{17}H_{35}$, Ph, PhO, or containing the diacetylene group -o-$(CO_2H)C_6H_4$.

—$OSO_2R_2$, wherein $R_2$ is Ph, p-$MeC_6H_4$, p-$FC_6H_4$, p-$CIC_6H_4$, p$BrC_6H_4$, p-$MeOC_6H_4$, m-$CF_3C_6H_4$, 2-$C_{10}H_7$, or Me —$CO_2^-M$, wherein M is H, $K^+$, $Na^+$ or $Ba^{2+}$.

The preferred materials which can be employed as head groups in the present invention are:

—$CH_2OCONHR_2$ or —$CH_2CONHR_2$ where $R_2$ is Et, n-Bu, n-$C_6H_{13}$, n-$C_8H_{17}$, n $C_{12}H_{25}$, cyclo $C_6H_{11}$, Ph, p-$MeC_6H_4$, m-$MeC_6H_4$, o-$CIC_6H_4$, m-$CIC_6H_4$, p-$CIC_6H_4$, o-$MeOC_6H_4$, 3-Thienyl, Me, Et, Ph, 1-$C_{10}H_7$, Et, Ph, $EtOCOCH_2$, $BuOCOCH_2$, Me, Et, i-Pr, n-$C_6H_{13}$, $EtOCOCH_2$, $BuOCOCH_2$, Ph, 2,4 $(NO_2)_2$ $C_6H_3OCH_2$, or $CH_2CH_2OH$.

The most preferred head groups are taken from —$CH_2COX$, where X is OH, MeO or any salt thereof.

Liqand Group The ligand group of the present invention can be of a wide variety of materials. The main criteria is that the ligand have an affinity for the analyte of choice. The ligand may be of a broad range, such as when a class of materials is to be assayed. Appropriate ligands include peptides, carbohydrates, nucleic acids or any organic molecules which bind to receptors. Thus, this molecule can successfully be employed to screen for all influenza strains, including those which have not yet been characterized.

A number of specific ligands which are naturally biomembrane associated have been effectively employed by some of the inventors to specifically detect analytes. These include sialic acid derivatives to detect influenza virus, $G_{M1}$ gangliosides to detect cholera toxin, and $G_{T1b}$ gangliosides to detect botulinum neurotoxin.

Figure 5A:
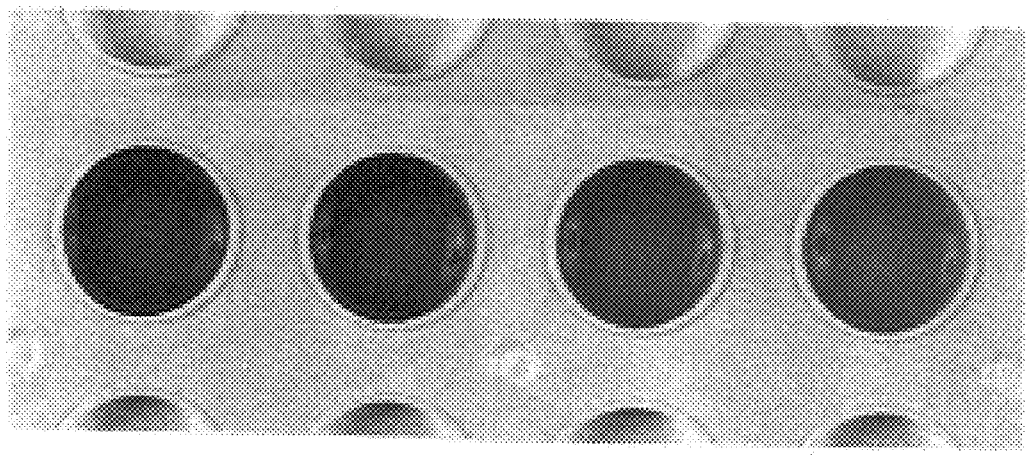
FIG. 5a is a color photograph of liposomes before and after addition of influenza virus.
Figure 5B:
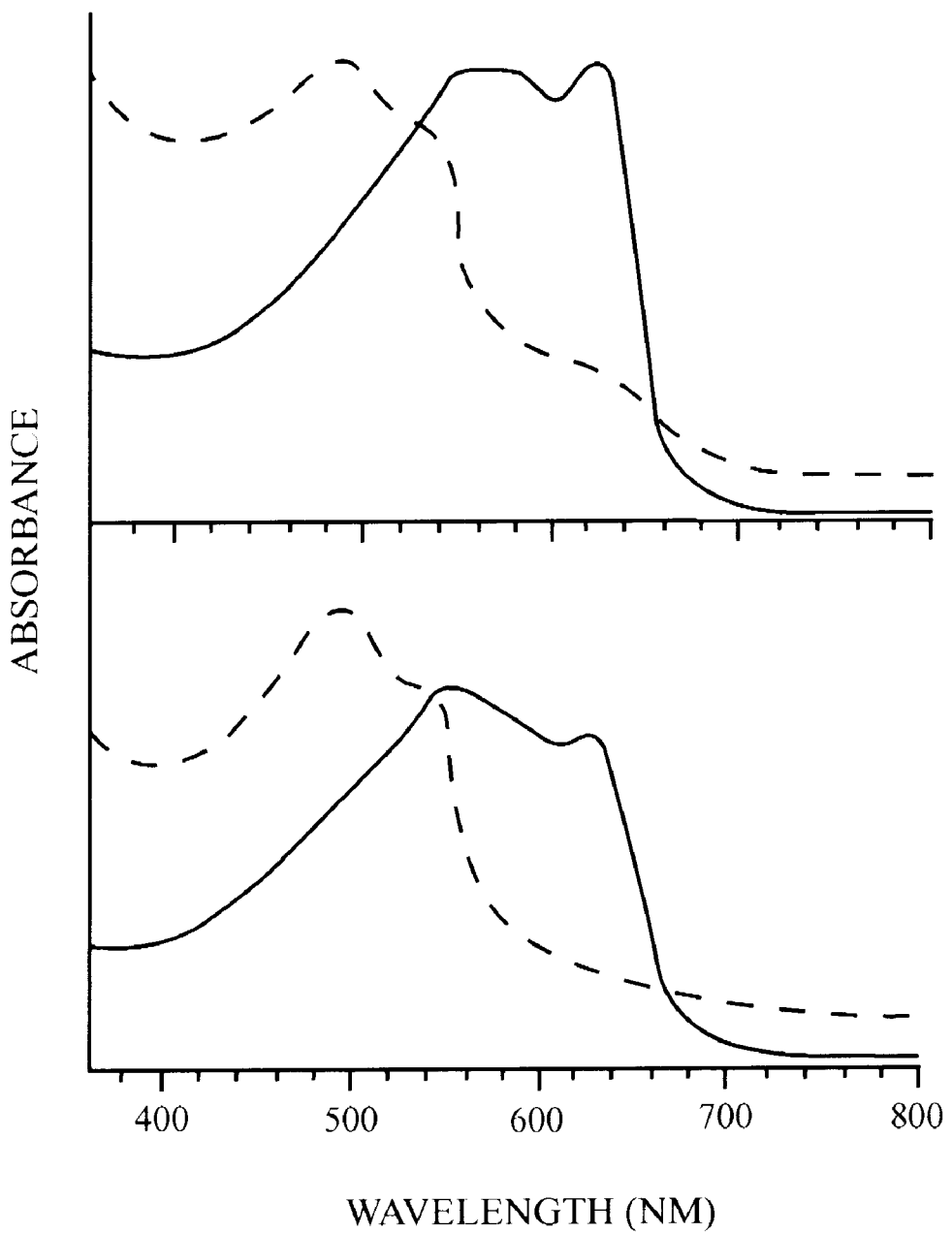

Ligands can also be used in the present invention when they function as competitive binders to the analyte. For instance, a pathogen could be introduced with a test material which is to be the presence of receptor molecule. In absence of this molecule, the pathogen will bind to the three-dimensional polymeric structure and produce a color. To the degree that the pathogen surface is bound to the receptor molecule introduced in the test material, the binding will be diminished. In this way, the presence of receptor molecule can be detected and quantified.

Receptor-Binding Molecules The use of ganglioside acid derivatives in one preferred embodiment described in the examples below is an example of the use of receptor-binding molecules in this capacity. Receptor-binding molecules are materials on the surface of a host cell to which a pathogen attaches itself as a prelude to the ineffective event. Selecting these molecules at the ligand group in the present invention has many advantages over other receptor molecules.

The recognition site for these molecules tend to be highly genetically conserved in the pathogen because of its obvious criticality to survival. Therefore, different strains of the same pathogen will generally not produce a false negative when such molecules are selected as the ligand group in the subject invention. Also, receptor molecules tend to be smaller and less complex than antibodies to the same analyte.

An increasing number of receptor molecules are being recognized, identified, isolated, and synthesized for a large number of pathogens. Many have been improved for use in various analytic and treatment systems. An example of this trend in research is the ganglioside derivative used in the example below of the subject invention.

Forms of the Liposomes The doped liposomes of the subject can in fact be produced in any number of forms. One of the most important forms which can be produced is the classic spherical liposome. Several methods for producing the subject liposomes into that particular form are fully set forth in the Example section of this application.

The more broadly defined liposomes of the subject invention can be formed in a number of different sizes and types. For instance, it is possible to form the liposomes as simple bi-layer structures. Additionally, they can be multi-layered, in an onion type structure. Their size can also be varied.

Numerous other shapes can also be produced. Double chains (Kuo et al, *Macromolecule*, p 3225, Vol. 23 1990), lamellae (Rhodes, et al *Lanqmuir*, p 267 Vol. 10, 1994), hollow tubules and braids (Frankel et al, *Journal of the American Chemistry Society*, Vol. 116, 1994), among other shapes can be formed.

One example of a successful protocol for producing the liposome embodiment of the subject invention is as follows:

mixing of the appropriate amounts of the chloroform solutions of the lipids (1–15 mM) in a small vial evaporation of the chloroform with a stream of nitrogen addition of the appropriate amount of de-ionized water (total lipid concentration 1–2 mM)

heating of the solution above the phase transition of the lipids (about 80–90° C.)

sonication of the solution for 15 minutes (probe sonicator, Fisher sonic dismembrator model 300, 50% maximum output, microtip)

filtration of the warm opaque solution through a 0.8 μm nylon filter (Gelman) to remove small titanium particles from the solution cooling of the solution for at least one hour up to one day in the fridge (4° C.)

removal of the oxygen in the solution by bubbling nitrogen through the sample for 5–10 minutes prior to polymerization polymerization of the stirred liposome solution in a 1 cm quartz cuvette with a small 254 nm UV-lamp (pen-ray, energy: 1600 μw/cm$^2$) in a distance of 3 cm in a small chamber which is purged with nitrogen 20 minutes prior to and during the polymerization to replace all oxygen and to cool the sample; polymerization times vary between 5 and 30 minutes depending on the desired properties (color, polymerization degree) of the liposomes.

Doped Monolaver Assemblages Predictive of Doped Colorimetric Liposome Characteristics To self-assemble the most sensitive layers to detect toxin binding, typically a mole ratio of 90% PDA, 5% sialic-acid-derivatized PDA and 5% ganglioside lipid is used. If more than 5% ganglioside is used, polymerization is reduced to such an extent that the films are of poor optical quality due to steric hindrance of the solid-state polymerization. For films containing the lactose promoter lipid, it was found that too high a concentration of lactose-derivatized PDA(>5%) also led to unstable films that turned red upon exposure to buffer solutions. In optimal conditions, the self-assembled monolayer of 2% lactose-derivatized PDA, 5% ganglioside and 93% PDA resulted in a blue to red color change when the film was incubated specifically with cholera toxin. When these materials are formed into liposomes, improved sensitivity will result.

Colorimetric detection of viruses and neurotoxins

FIG. 3 is a figured representation of the construction of heterogeneously polymerized thin-film assemblies for the detection of toxins. Films were assembled from a starting solution of an organic mixed solvent (chloroform; methanol 2:1) containing 2–5% sialic-acid- or lactose-derivatized PDA (compound 2 or 3), 90–93% PDA (compound 1) and 5% ganglioside $G_{M1}$ or $G_{T1b}$ (compound 4 or 5) as shown in the example section. After polymerization, the film displays a steady blue color, but upon exposure to toxin the film turns red.

The inventive biosensor films obtained exhibit the characteristic blue color due to the presence of conjugated, planar, rigid polydiacetylene chains in the molecular assembly. This is demonstrated in FIG. 4 which provides calorimetric, spectrophotometric, and titration data for cholera toxin biosensor with the $G_{M1}$ ganglioside. FIG. 4*a* shows photos of untreated $G_{M1}$ sensor placed on silanized glass cover slides (left) which is blue, but minutes after exposure to 40 ppm cholera toxin is red (right). FIG. 4*b* provides the UV-VIS spectra of 5% $G_{M1}$, 5% sialic acid-PDA, 90% PDA sensor before (left) and after (middle, immediately after; right, 30 min. after) exposure to 40 ppm cholera toxin. FIG. 4*c* is a plot of the calorimetric response of the biosensor used in FIG. 4*b* as a function of cholera toxin concentration in ppm. Each point in the graph is the average value of four measurements, with the standard deviation as the error.

The results from these doped materials can be compared with the color of the liposome sensor for influenza virus and will be predictive of the materials characteristics when assembled in liposome form. FIG. 5 shows the calorimetric detection of influenza virus using polymerized liposomes containing sialic acid. FIG. 5*a* is a photograph of liposomes to which have been added increasing amounts (from left to right) of influenza virus. Liposomes were 5% sialic acid-PDA and 95% tricosadiynoic acid. To each well was added the following amounts of influenza virus (left to right): O HAU, 8 HAU, 16 HAU, 32 HAU. FIG. 5b is the visible absorption spectra before (solid line) and after (dashed line) incubation with influenza virus starting with either a blue liposome solution (top, 8 min UV treatment) or pure liposome solution (bottom, 24 min UV treatment). The concentration of the liposome solutions in PBS buffer was 0.13 mM. The solution was incubated with 60 HAU of influenza virus for 1 h.

Figure 4A:
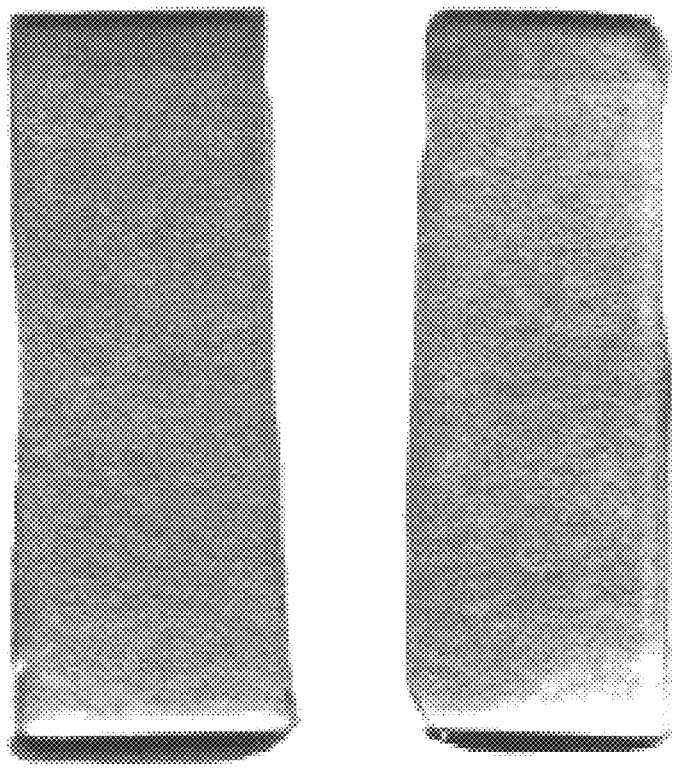
FIG. 4a is a photograph showing doped film before and after exposure to cholera toxin.
Figure 4B:
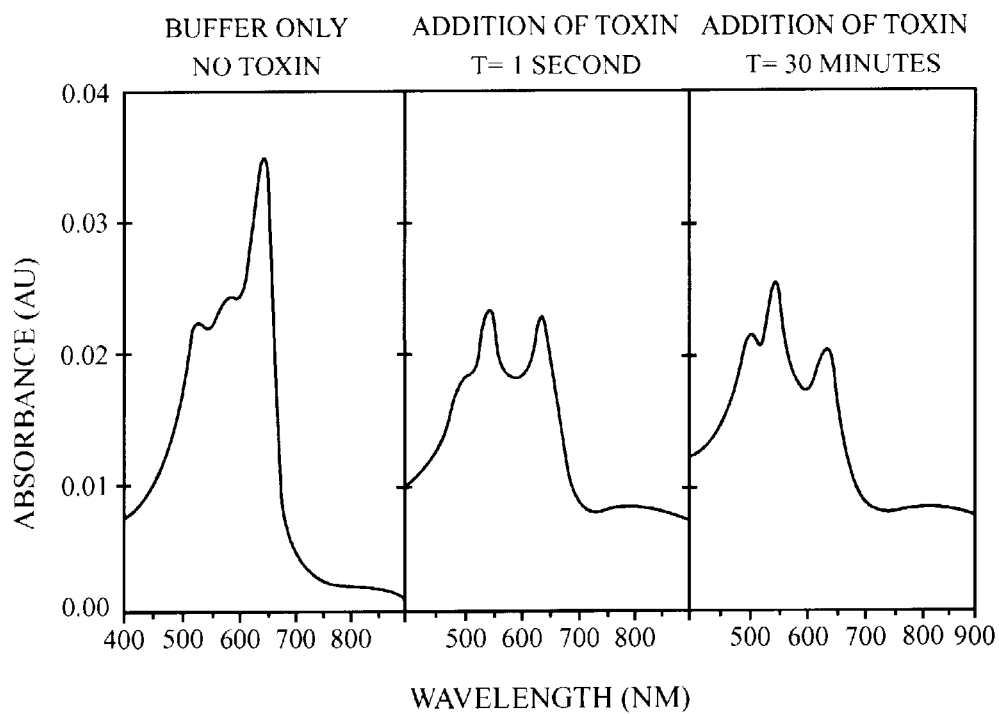

The optical properties of these sensors can be quantified by visible absorption spectroscopy (FIGS. 4b, 5b). For example, the blue colored film has an absorption maximum of ~630 nm and a weaker absorption at ~550 nm. After incubation with the target analyte a dramatic change in the visible spectrum occurs. The maximum at ~550 nm increases with a concurrent decrease in the maximum at ~630 nm, and the film or liposome suspension appears red. The color change can be quantified by calculation of the colorimetric response (CR) by measuring the relative change in the percentage of the intensity at ~630 nm relative to the intensity at ~550 nm. When these materials are assembled in liposome form, more sensitivity will be achieved over undoped liposomes.

Figure 4C:
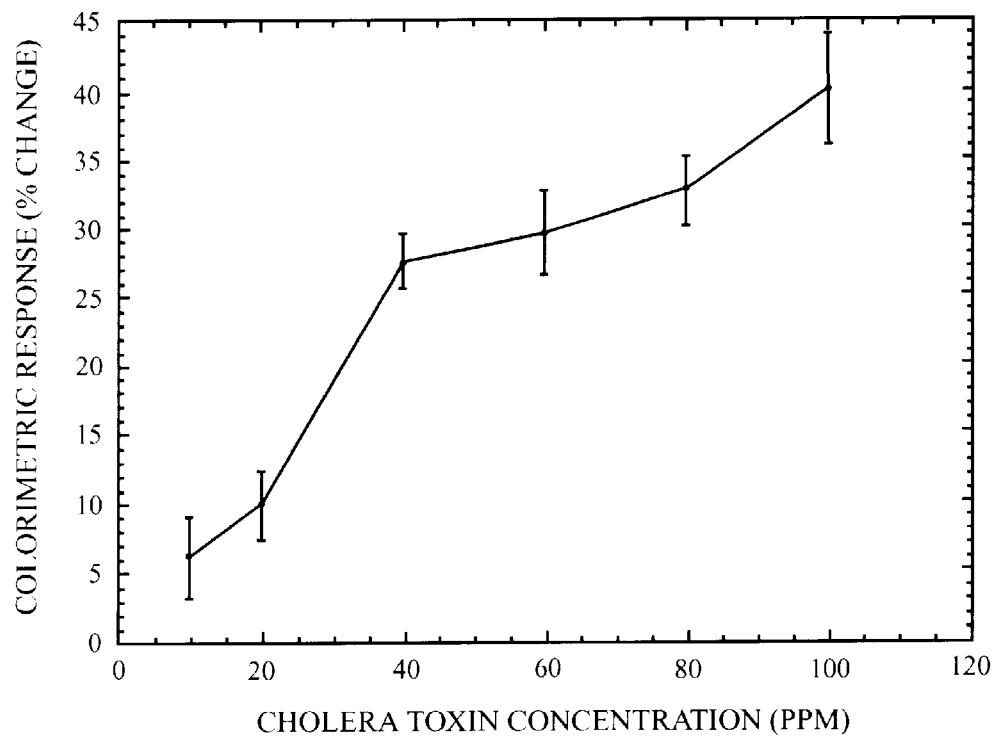
FIG. 4c is a graph showing the calorimetric response as in FIG. 4a as a function of cholera toxin concentration.

To determine the sensitivity of the biosensors to target analyte, the response (CR) of the sensor as a function of analyte concentration was determined (FIG. 4c). In agreement with previous results, the CR is directly proportional to the quantity of target analyte. For the $G_{M1}$-containing biosensor, the calorimetric response to cholera toxin rises steeply at low toxin concentration, then levels out at higher concentration, indicating that surface binding sites are saturated (FIG. 4c).

The low detection limit corresponds to a sensitivity of $\sim 1 \times 10^{-10}$ M. The absolute sensitivity of the lactose-derivatized PDA doped film is slightly lower than that of films containing the sialic acid promoter lipid, due to the higher background level in the presence of buffer only (CR=7% for lactose-PDA; CR=5% for sialic acid-PDA). Similar results are seen using the $G_{T1b}$ ganglioside biosensor and botulinum neurotoxin, and using the $G_{M1}$ ganglioside biosensor to detect E. coli enterotoxin.

To demonstrate that the incorporation of $G_{M1}$ into the biosensor assembly did not compromise the $G_{M1}$-cholera toxin interaction, the supramolecular array was self-assembled onto a gold chip, and the interaction was measured by surface plasmon resonance using a Biacore 2000 instrument. The binding affinity ($K_a$) of cholera toxin to the $G_{M1}$ biosensor was determined to be $3 \times 10^{10}$ M$^{-1}$, in agreement with the published values observed in vivo. This suggests that $G_{M1}$ incorporated into the artificial membrane behaves similarly to $G_{M1}$ on the surface of living cells.

To evaluate the selectivity of the sensor material, a series of experiments were carried out to confirm that the functionalized polydiacetylene assemblies are specific to the biological target. For example, *Escherichia coli cell* lysate, bovine serum albumin, pertussis toxin, diphtheria toxin, and various buffers at different salt and pH conditions produce a background CR of ~5%; the highest background was seen using bovine serum albumin (BSA).

Figure 6A:
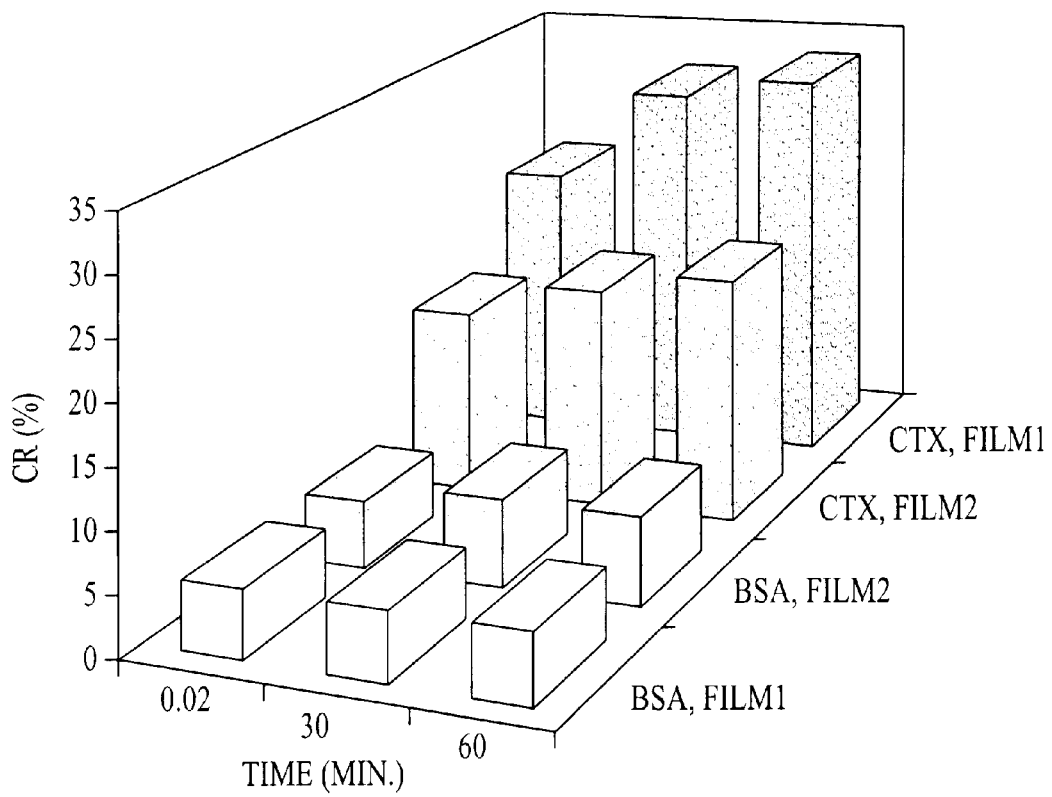
FIG. 6a is a three-dimensional graph comparing various films colorimetric response over time to toxin or bovine serum.

FIG. 6 documents control experiments to determine the selectivity of sensors. FIG. 6a shows that either film 1 (5% $G_{M1}$, 5% sialic acid-PDA, 90% PDA) or film 2 (5% $G_{M1}$, 2% lactose-PDA, 93% PDA) were used to measure the calorimetric response to the addition of bovine serum albumin (BSA, 40 ppm) or cholera toxin (CTX, 40 ppm final) at time 7s (0.02 min), 30 min, and 60 min. The calorimetric response did not change significantly after 60 min.

Figure 6B:
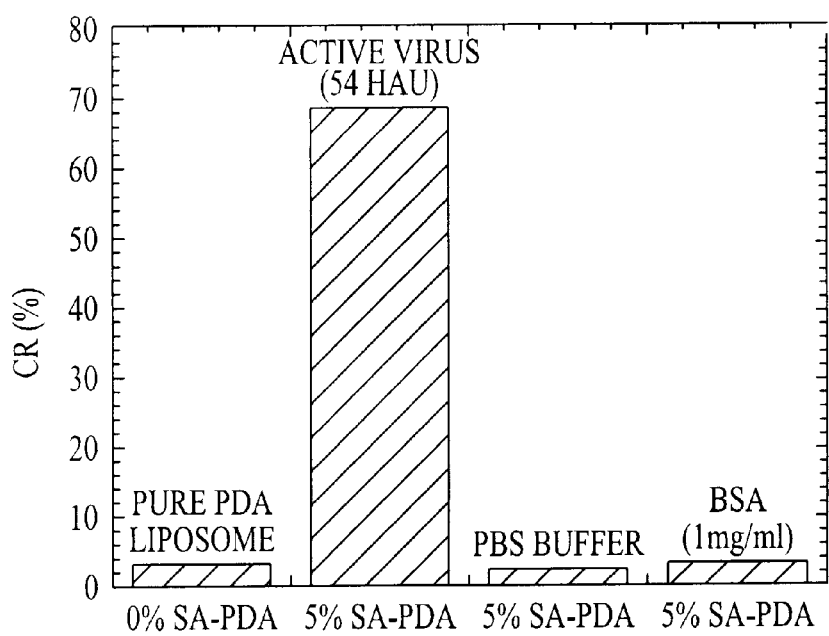
FIG. 6b is a bar graph showing color changes in response to viral control samples.

Other neurotoxins and BSA were used to determine the selectivity of the toxin sensor, but only BSA is illustrated here, since it induced the largest response out of all the negative controls. FIG. 6b shows results of virus controls with liposomes. No color change could be observed after the addition of 54 HAU of virus if the sialic acid lipid was removed from the molecular assembly (column 1). Column 2 shows the response of liposomes that contain the sialic acid ligand to 54 HAU of virus. Column 3 shows background CR seen in response to PBS buffer only, and 1 mg/1 ml bovine serum albumin are also shown. These results define the level of non-specific adhesion, and therefore, the minimum detection limit.

Low levels of toxin or virus molecules yield CRs significantly above the background level (FIG. 6). No cross reactivity was observed between the neurotoxin and virus sensors. The majority of the calorimetric response occurs immediately upon exposure to the target analyte. After one second, 75% of the total CR to target analyte is observed to occur (FIG. 6a).

Production of Doped Colorimetric Liposomes A much higher concentration of polymerized material can be achieved with liposome solutions compared to monolayer assemblies (FIG. 1), due to their greater cross-sectional density. Liposomes have the advantage of making the color change more visually striking and increasing the calorimetric response (compare FIGS. 4, 5).

The liposomes are prepared from the same starting monomers as would be used for thin film assembly, typically using a probe sonication method. The optical absorption properties of the liposomes can be controlled to a certain extent by the polymerization time (FIG. 5b). Typically, blue liposomes turn pink, while purple liposomes turn orange upon addition of target analyte. As noted with the neurotoxin sensors, the calorimetric response increases with increasing amounts of analyte. No color change could be detected if pure PBS buffer (phosphate buffered saline) or a solution of bovine serum albumin (BSA) in PBS buffer (1 mg ml$^{-1}$) was added to the virus sensor system (FIG. 6).

The amount of virus that can be detected above the background is 8 hemagglutination units (HAU). One HAU is defined as the highest dilution of stock virus that completely agglutinates a standard erythrocyte suspension, and 8 HAU corresponds to $\sim 8 \times 10^7$ virus particles. As illustrated in FIG. 6, the liposome sensor produces a much higher response to virus binding than the thin film sensor does for toxin binding. Typically, the liposome sensors have CR values of ~70%, relative to typical thin-film CR values for toxins of ~30%.

The specific nature of the interaction between the influenza virus and the sialic acid-PDA liposomes was confirmed by a competitive inhibition experiment. In the presence of α-O-methyl neuraminic acid, a known inhibitor of influenza virus hemagglutinin, no color change is observed. Therefore, the color transitions seem to be induced by specific binding of biological targets to the membrane-like surface. This methodology is useful for detecting a wide variety of potential antiviral or antitoxin drugs in a high-throughput screening format.

The role of the "promoters" dopant molecule (either sialic-acid- or lactose-derivatized PDA) in the ternary film assembly has not been firmly established. It appears that the promoter does not function in the molecular recognition event itself (as if the receptor is omitted from the assembly there is no colorimetric change), but may serve to decrease the activation barrier for the blue to red transition. One theory of the inventors is that the bulky sugar headgroup in the promoter is subject to various solvent interactions at the matrix surface, destabilizing the structure of the blue film and thus allowing the relatively small perturbations provided by the toxin to complete the calorimetric transition. Since the gangliosides are not covalently connected to the PDA backbone, it also seems possible that the steric effects induced by the molecular recognition event may interfere with the headgroups of the promoter lipid, thus propagating the changes resulting from recognition to the chromatic unit of the sensor.

EXAMPLE 1

Construction of thin Film Assemblies for the Detection of Toxins

To construct heterogeneously polymerized thin film assemblies to detect toxins, an organic mixed solvent (chloroform:methanol 2:1) containing 2–5% sialic-acid- or lactose-derivatized PDA (FIG. 2 compound 2 or 3), 90–93% PDA (FIG. 2 compound 1), and 5% $G_{M1}$ or $G_{T1b}$ (FIG. 2 compound 4 or 5) was dispersed onto the surface of a Langmuir-Blodgett (LB) trough from RSV (Helsinki, Finland) containing $1\times10^{-3}$ M $Cd^{2+}$ as the subphase.

The substances were equilibrated at room temperature for 30–60 min to allow organic solvent to evaporate, compressed to the solid-analogous phase, and transferred to the glass slides pre-coated with octadecyltrichlorosilane through vertical dipping at the speed of 5 mm min$^{-1}$. The resulting LB films were polymerized 1 min per side with a UVP mineralight (Fisher). After polymerization, the film displays a steady blue color.

EXAMPLE 2

Colorimetric and Spectrophotometric Detection of Cholera Toxin Binding

Toxin binding studies were carried out with the biosensor containing $G_{M1}$ ganglioside in a buffer consisting of 50 mM Tris, 200 mM NaCl, 1 mM EDTA and 3 mM NaN$_3$, pH 7.4. The films were first incubated in the buffer solution; films remaining in the buffer served as the background reference when toxins were added to generate a color change. The color change could be detected visually and was quantified using a Perkin-Elmer Lambda 11 UV—VIS spectrometer.

The response time was studied by monitoring the spectra of the biosensor immediately after the film was exposed to a solution containing 40 ppm cholera toxin. Three time points were taken to measure to colorimetric response; is (0.02 min), 30 min and 60 min. The calorimetric response did not change significantly between 1 h and 24 h. The dynamic response range of the cholera toxin biosensor was determined with the film containing 5% $G_{M1}$ ganglioside, 5% sialic acid-PDA and 90% PDA as a function of cholera toxin concentration in ppm.

EXAMPLE 3

Construction of Sialic-acid-derivatized Diacetylene Liposomes for Detection of Influenza Virus Lipids (compounds 1 and 2) were mixed in chloroform in a test tube, and the organic solvent was evaporated to yield a thick film of the lipids on the glass. An appropriate amount of deionized water was added to give a total lipid concentration of 1 mM. The sample was heated to 80° C., and sonicated for 15 min. The warm solution was filtered through a 0.8 mm nylon filter to remove undispersed lipid, and then cooled to 4° C.

Prior to polymerization, the liposome solution was purged with N$_2$ for 5 min after warming to ambient temperature. The polymerization was achieved by irradiating the solution with a UVP lamp (~254 nm) at a distance of 3 cm with varying irradiation times.

EXAMPLE 4

Colorimetric Detection of Influenza Virus

In the wells of a ELISA plate, 200 μl of phosphate buffered saline (PBS, pH 7.4) was mixed with 30 μl of the liposome solution (5% compound 2, 9% compound 1). The reaction was started by adding the appropriate amount of influenza virus (in most cases, 30 μl), PBS as a reference, or BSA in PBS (1 mg ml$^{-1}$). UV spectra were recorded after various times until the color of the liposome/virus solution was unchanged.

EXAMPLE 5

Control Experiments to Determine the Selectivity of Toxin Sensors

Cholera toxin (CTX), bovine serum albumin (BSA) and a variety of other neurotoxins (including pertussis toxin and diphtheria toxin) were used to determine the selectivity of the toxin sensor (all toxins used at 40 ppm). Only BSA is illustrated as a negative control in FIG. 6, since BSA induced the largest response of all of the negative controls. The response of both Langmuir-Blodgett films and liposomes were studied, with either sialic acid-PDA or lactose-PDA. No color change could be observed if the sialic-acid lipid or lactose lipid was removed from the molecular assembly.

EXAMPLE 6

Inhibitor Control Experiments to Block Virus Binding

In a microtiter plate well, 20 μl of virus solution (54 HAU), 100 μl of PBS buffer and 50 μl of inhibitors in PBS (100 mM α-O-methyl neuramanic acid) were mixed and preincubated for 1 h at room temperature. In two other wells, 150 μl of PBS buffer was mixed either with 20 μl of active virus or 20 μl of buffer. To start the reaction, 20 μl of the liposome solution (10% sialic acid-PDA) was added to each well. Again, the changes in UV spectra were monitored over time.

We claim:

1. A composition comprising doped liposomes that change color in the presence of an analyte, wherein said doped liposomes comprise: a) a plurality of polymerized diynes; b) one or more ligands having an affinity for said analyte; and c) a dopant having no affinity for said analyte.

2. The composition of claim 1, wherein said one or more ligands are selected from the group consisting of epidermal growth factor, acetylcholine receptor, complement receptor, beta-adrenergic receptor, ICAM-1, polio virus receptor, trisaccharide, tetrasaccharide, ganglioside $G_{M1}$ and ganglioside $G_{T1b}$.

3. The composition of claim 1, wherein said one or more ligands are noncovalently incorporated into said liposomes.

4. The composition of claim 1, wherein said dopant has a molecular weight of 30 to 2,500 atomic mass units.

5. The composition of claim 4, wherein said dopant has a molecular weight of 50 to 1,000 atomic mass units.

6. The composition of claim 1, wherein said dopant is 0.01–75% of the total mass of said liposomes.

7. The composition of claim 6, wherein said dopant is 2–10% of the total mass of said liposomes.

8. The composition of claim 7, wherein said dopant is 5% of the total mass of said liposomes.

9. The composition of claim 1, wherein said dopant is a surfactant.

10. The composition of claim 9, wherein said surfactant is selected from the group consisting of polysorbate, octoxynol, sodium dodecyl sulfate, polyethylene glycol, zwitterionic detergents, peptide detergents, 3-[3-(cholamidopropyl)dimethylammonio]-1-propanesulfonate, decylglucoside, and deoxycholate.

11. The composition of claim 1, wherein said dopant is a diacetylene derivative.

12. The composition of claim 11, wherein said diacetylene derivative is selected from the group consisting of sialic acid derivated diacetylene, and lactose derived diacetylene.

13. The composition of claim 1, wherein said dopant is a lipid.

14. The composition of claim 13, wherein said lipid is selected from the group consisting of phosphatidylserine, phosphatidylinositol, phosphatidylethanolamine, phosphatidylcholines, phosphatidylglycerol, phosphatidic acid, phosphatidylmethanol, cardiolipin, ceramide, cholesterol, cerebroside, lysophosphatidylcholine, D-erythrosphingosine, sphingomyelin, dodecyl phosphocholine, and N-biotinyl phosphatidylethanolamine.

15. A method of making doped colorimetric liposomes that change color in the presence of an analyte, comprising the steps of:
  a) providing:
    i) a plurality of diyne monomers,
    ii) one or more ligands having an affinity for said analyte,
    iii) a dopant having no affinity for said analyte,
    iv) one or more organic solvents, and
    v) an aqueous solution;
  b) combining said diyne monomers, said dopant, said one or more ligands, and said one or more organic solvents to form an organic mixture;
  c) evaporating said one or more organic solvents in said organic mixture to produce a concentrated mixture;
  d) adding said aqueous solution to said concentrated mixture to produce an aqueous mixture;
  e) heating said aqueous mixture above the main-phase transition temperature of said diyne monomers;
  f) agitating said aqueous mixture to produce an agitated mixture;
  g) cooling said agitated mixture to at least about 4° C. to produce doped liposomes; and
  h) polymerizing said doped liposomes to produce doped liposomes capable of changing color in the presence of an analyte.

16. The method of claim 15, wherein said agitating comprises sonication.

17. The method of claim 15, wherein said one or more organic solvents are selected from the group consisting of chloroform, benzene, alcohol, cyclohexane, hexane, methylene chloride, acetonitrile, and carbontetrachloride.

18. The method of claim 15, wherein said aqueous solution is selected from the group consisting of water, buffer solution, cell media, physiological saline, phosphate buffered saline, Trizma buffer, N-[2-hydroxyethyl]piperazine-N'-[2-ethanesulfonic acid], and 3-[N-morpholino] propanesulfoni acid.

19. The method of claim 15, further comprising filtering said agitated mixture in step f) before cooling in step g).

20. The method of claim 15, further comprising removing oxygen in said doped liposomes in step g) before polymerizing in step h).

21. Doped liposomes made according to the method of claim 15.

* * * * *